United States Patent [19]

Pfirrmann

[11] Patent Number: 4,587,268

[45] Date of Patent: May 6, 1986

[54] TREATMENT OF OSTEITIS

[75] Inventor: Rolf W. Pfirrmann, Lucerne, Switzerland

[73] Assignee: Ed. Geistlich Sohne A.G. fur Chemische Industrie, Lucerne, Switzerland

[21] Appl. No.: 587,707

[22] Filed: Mar. 8, 1984

Related U.S. Application Data

[63] Continuation of Ser. No. 298,889, Sep. 2, 1981, abandoned.

[30] Foreign Application Priority Data

Sep. 3, 1980 [GB] United Kingdom ................ 8028482

[51] Int. Cl.$^4$ ...................... A01N 25/00; A01N 63/02
[52] U.S. Cl. ...................................... 514/774; 424/95; 514/222
[58] Field of Search .................... 424/177, 37, 95, 359, 424/36, 19, 28; 604/891; 260/117; 3/1.9; 514/774, 222

[56] References Cited

U.S. PATENT DOCUMENTS

| | | | |
|---|---|---|---|
| 3,325,366 | 6/1967 | Blaug et al. | 424/28 |
| 3,400,199 | 9/1968 | Balassa | 424/95 |
| 3,520,949 | 7/1970 | Sheperd et al. | 525/426 |
| 3,703,575 | 11/1972 | Thiele | 424/27 |
| 3,966,908 | 6/1976 | Balassa | 424/95 |
| 4,011,312 | 3/1977 | Reuter et al. | 424/78 |
| 4,093,576 | 6/1978 | de Wijn | 424/78 X |
| 4,191,747 | 3/1980 | Scheicher | 424/180 X |
| 4,233,360 | 11/1980 | Luck et al. | 424/28 X |
| 4,291,013 | 9/1981 | Wahlig et al. | 424/28 X |
| 4,349,470 | 9/1982 | Battista | 424/360 X |

Primary Examiner—Esther M. Kepplinger
Assistant Examiner—Shawn P. Foley
Attorney, Agent, or Firm—Bernard, Rothwell & Brown

[57] ABSTRACT

A composition comprising a resorbable aqueous gel having dissolved or dispersed therein one or more water-soluble medicaments is of use in the treatment of wounds.

Such a composition is of use in a method of healing an infection in a cavity in bone or other tissue whereby the resorbable aqueous gel is placed in the cavity and allowed to remain there until resorbed, the aqueous phase of the gel containing the water soluble medicament.

The medicament is preferably an antibiotic or a methylol transfer antibacterial.

9 Claims, No Drawings

TREATMENT OF OSTEITIS

This is a continuation of application Ser. No. 298,889 filed Sept. 2, 1981, now abondoned.

"Treatment of Osteitis"

This invention concerns a method of treating osteitis and related diseases and compositions for use in such treatment.

Osteitis, sometimes known as osteomyelitis, is a disease of the bone marrow caused by bacterial infection; typical forms are haematogenic osteitis, posttraumatic osteitis and infected osteosynthesis. Once the bone has been infected, it is extremely difficult to cure and, indeed, osteitis is characterised by relapses occurring long after apparent healing. This difficulty has long been recognised and, indeed, operations against osteitis date back to classical times and even earlier. Even with advent of antibiotics, no really satisfactory permanent cure for osteitis has been developed. Similar difficulties are often encountered in treating abcesses creating large cavities.

In the treatment of osteitis, removal by surgery of necrotic tissue (for example the avitale sequestrum) and bacterially infected tissue with simultaneous systemic treatment with antibiotics is, as a rule, not sufficient. It is necessary to employ methods capable of providing a high local concentration of antibiotics over a period of time sufficient to allow healing.

Local drainage of the osteitic cavity has hitherto been employed as a supplementary therapeutic measure. However, this method is not always fully effective and leads to a long period when the patient is bedridden with restricted freedom of movement and experiences severe pain. This method also necessitates high expenditure on nursing care.

It has previously been proposed to treat osteitis by inserting into an osteitic cavity a chain of polymethylmethacrylate balls impregnated with the antibiotic gentamycin. When such a method is used, removal of the balls can have drastic effects on new tissue which has formed in the cavity. Unfortunately, the mass of fresh spongiosa and connective tissue closely surrounds the individual balls of the chain and although these are laid in the cavity in such a way that the chain can be pulled out through the mass, considerable painful damage is inevitably caused to the newly grown tissue, with adverse effects on healing. Furthermore, gentamycin is the only antibiotic which has been found to withstand the polymerisation conditions but it has the disadvantage of possessing a high resistance ratio in relation to osteitis and this leads to a higher rate of recurrence of the disease.

We have found that instead of designing the slow release carrier for the antibacterial substance to be removed, it is advantageous for the carrier to be resorbable, so that it does not need to be removed in a second operation. In particular, we have found that an aqueous gel formed from cross-linked fibrous protein provides a particularly good resorbable carrier.

One embodiment of the invention, therefore, provides a method of healing an infection in a cavity in bone or other tissue whereby a resorbable, aqueous gel, the aqueous phase of which contains a water-soluble medicament, such as an antibacterial compound, is placed in the cavity and allowed to remain therein until resorbed.

In a particularly preferred embodiment of the invention, however, the gel is relatively rapidly resorbed, for example over a period of a few weeks, advantageously 10 to 14 days, the active antibacterial substance being released primarily by the resorption process rather than by diffusion of the antibacterial substance out of the gel.

The gel may be in the form of a shaped solid, such as a rod, for insertion into the cavity to be healed, thus possibly being 2 to 20 mm in diameter and 20 to 150 mm in length. In a particularly advantageous embodiment of the invention the gel is in the form of a granulate. Using this form it is possible to fill completely cavities of any shape or size without the need for implants of specialised configurations.

The rapidly resorbable gel is preferably an aqueous gel of a cross-linked, water soluble fibrous protein, e.g. a scleroprotein such as tropocollagen or partially hydrolysed collagen, tropocollagen or elastin (including, in particular, gelatin). Elastin is the elastic fibrous protein of tendons and arteries. Collagen is the inelastic fibrous protein of skin, tendons and bones, and consists of strands of molecules of tropocollagen in a triple helix configuration. The tropocollagen can be liberated, for example from the skin of young mammals, by extraction with citrate buffer. The molecular weight of the partially hydrolysed collagen, tropocollagen or elastin is preferably in the range 100,000 to 350,000. When boiled in water, collagen yields the protein gelatin.

In general, the resorbable gel preferably contains gelatin, even when other fibrous proteins are present. This ensures flexibility in the gel and avoids undue rigidity which in some cases could cause problems in inserting the gel into the cavity to be healed. Where a high degree of flexibility is advantageous, for example where the gel is in the form of a three dimensional shape such as a rod, the gel preferably contains 80% to 100% by weight of gelatin, advantageously substantially 100%. Where the gel is provided in the form of a granulate the degree of flexibility must however be balanced by a certain degree of firmness so as to allow proper granulation. In this case certain quantities of fibrous proteins other than gelatin may be used and the gelatin content may, for example, be in the range 60% to 80%, e.g. about 70% by weight of total protein, the remainder being tropocollagen or partially hydrolysed collagen, tropocollagen or elastin or, if desired fibres of unhydrolysed collagen or elastin. Naturally, such granulates can, if desired, contain higher quantities of gelatin, and 100% gelatin may be used, if sufficiently cross-linked.

The properties of gelatin may be influenced by its mode of manufacture. So called edible gelatin is made by the acid hydrolysis of skin collagen and it is found to give a pH of about 4.2 on dispersion in water. 'Bone gelatin', on the other hand, is often prepared by alkaline hydrolysis of bone collagen and on dispersion in water gives a less acidic pH e.g. about 6.0. We have found that on reaction with equal amounts of cross-linking agent, the less acid bone gelatin gives a firmer more resilient gel than does the more acidic edible gelatin. However, it may be preferable to neutralise the gelatin solution e.g. to about 7.0 prior to cross-linking, in order to make the gel more completely physiologically compatible.

The fibrous protein preferably comprises 5 to 30% by weight of the gel, advantageously about 10–20%, depending on the properties desired. The gel preferably remains solid at body temperatures but this is not essential. Thus, for example, when the gel is relatively hard, resorption is slower. This can be achieved by using more formaldehyde. Similarly, if faster resorption is desired, a softer gel may be appropriate. Harder gels may be preferable where granulates are required in that they are more readily mechanically granulated.

The gels can also contain other additives which desirably influence their physical and/or biochemical properties. One useful such additive is calcium phosphate which has the effect of improving the firmness of the gels. Furthermore, it is believed that the calcium phosphate may act to supply calcium to the bone by sustained release when the gel is in place in the cavity. Polysaccharides and polyvinyl-pyrrolidone, particularly of higher molecular weight, e.g. about 40,000, also may provide slower resorption.

Resorbable aqueous gels, for example gels based on cross-linked water-soluble fibrous protein such as gelatin, collagen or elastin, and having dissolved or dispersed therein one or more water soluble medicaments such as antibacterial agents, are new and form a further feature of the invention. Such gels are advantageously provided in granular form.

The antibacterial substances employed may be antibiotics and other microbiocidal or microbiostatic substances. In addition, further medicaments, for example analgesic agents, which are soluble in the swelling water of the gels may be used. In addition, the swelling water can also contain other dissolved additives which promote healing of the wound and/or favourably influence the physical and biochemical properties of the gel. These are, for example, amino acids, sugar, polyhydric alcohols, common salt and others. Finally, the gels can also contain an X-ray contrast agent.

When the antibacterial substance is an antibiotic, it is preferably a broad spectrum antibiotic active against both gram-negative and gram-positive bacteria, for example a β-lactam antibiotic such as a penicillin or cephalosporin, a tetracycline antibiotic, a macrolide antibiotic such as erythromycin, a polypeptide antibiotic such as bacitracin, novobiocin, or, more preferably, an aminoglycoside antibiotic such as streptomycin, neomycin, lincomycin, kanamycin, vancomycin, gentamicin or sisomycin. Typical infecting bacteria include *Staphylococcus aureus*, Proteus, Pseudomonas, Streptococcus, *E. coli*, as well as Enterococci, Klebsiella and *Staphylococcus albus*. However, antibiotics are often contraindicated for use in surgical treatment, due to their tendency to produce resistant strains, and a preferred type of antibacterial substance is a methylol transfer agent, especially noxytiolin or, more preferably taurolidine or a close analogue thereof. Taurolidine is bis-(1,1-dioxo-perhydroxy-1,2,4-Thiadiazin-4-yl) methane and this compound and its close analogues can be represented by the formula:

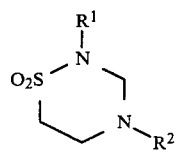
(I)

where $R^1$ is hydrogen or a methyl, ethyl, propyl, butyl or pentyl group and $R^2$ is hydrogen or a group

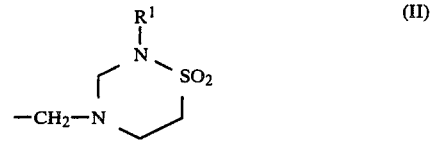
(II)

where $R^1$ has the above meaning. Where $R^1$ and $R^2$ are both hydrogen, the compound is the methylol transfer antibacterial Taurultam.

The preferred active substances are broad spectrum antibiotics and methylol transfer agents such as taurolidine. Taurolidine and its analogues are active against both gram-negative and gram-positive organisms, as well as against the toxins produced by gram-negative bacteria. Where taurolidine is used, its concentration in the aqueous solution absorbed in the gel is preferably 0.5% to 5% by weight, e.g. about 1 to 4%. Where the gel is in the form of a granulate, 2% taurolidine is preferred for use in large cavities. In small cavities, e.g. in the wrist, 4% taurolidine is preferred. Taurolidine is only about 3% soluble in water at room temperature, so that at higher concentrations, some material will be present as a suspension. Where gentamicin is used, its concentration is preferably in the range 0.05 to 0.2% by weight, for example about 0.1%.

The complex of elemental iodine and polyvinyl pyrrolidone may also be advantageously be used as a microbiocidal substance.

Cross-linking of the fibrous protein is necessary to ensure the cohesion of the gel and also serves to reduce immunological reactions to the "foreign" protein by reacting with free amino groups. The preferred cross-linking agent is a methylol transfer agent such as formaldehyde or a methylol transfer agent derived from formaldehyde, such as the antibacterial taurolidine. In general, using formaldehyde as the cross-linking agent, the percentage of bound formaldehyde in the gel relative to protein is preferably in the range 2.0 to 5.0, advantageously 2.3 to 4.0. Thus, for example, using 10% aqueous gelatin, it is convenient to add initially about 3.6% formaldehyde, the level of bound formaldehyde falling, after washing, to about 2.7%. However, if only about 2.7% formaldehyde is added initially, subsequent washing may often be dispensed with.

The gels according to the invention have been found to have the advantage of a surprising degree of resistance to bacterial infection. It is thought that this may be connected with the use of formaldehyde or its derivatives as a cross-linking agent. Although no free formaldehyde is present in the final product, the cross-linked protein material can to some extent function as a methylol transfer agent similar to taurolidine, so having some antiseptic action itself. Furthermore, the invention allows cross-linked gels to be provided which employ no toxic cross-linking agents such as those used for cross linking some other polymeric materials. This means that there is no risk of residual amounts of toxic substances being present in the gels when they are placed in the bone cavity. Because the gels according to the invention are resorbable, they have the advantage that only one operation should be necessary in the treatment of a given case of osteitis. Once the cavity has been filled with the gel the wound can be closed and should not need to be opened again. It has been found in practice that postoperative exudation from the wound is very quickly sterile and wound healing is generally free from complications. There is a high incidence of per primum healing.

Where the gel is cross-linked using formaldehyde, it is conveniently prepared by warming an appropriate quantity of the gel-forming protein in an aqueous solution of the active antibacterial substance, and any other desired components, to dissolve the protein and then adding formaldehyde, preferably in aqueous solution or in the form of a polymer of formaldehyde such as paraldehyde. Formalin, which is a 36–40% aqueous solution of formaldehyde, is especially convenient. Where gelatin is used, this may be for example edible gelatin or bone gelatin. As indicated above, bone gelatin generally gives a harder or firmer gel than edible gelatin. Generally, per 100 g of aqueous solution, containing e.g. 0.3–4.75 g of taurolidine, 7.0–12.0 g, e.g. 10.0 g of gelatin will be used, optionally with 1–35, e.g. 25 g of dibasic calcium phosphate. The aqueous solution may contain, in addition to taurolidine, such additives as gentamycin sulphate, chondroitin sulphate, and polyvinylpyrrolidone; finely ground bone powder may also be added if desired. Generally about 0.75–1.0 g of about 36% aqueous formaldehyde will be used in such a mixture. The solution is then poured into one or more preheated moulds, for example a length of tubing, and allowed to cool. After cooling and setting, the gel may, if required, be cut into suitably sized sections, and these may be granulated if desired by means of a conventional granulating machine or mincer. The granulate should generally be of average diameter in the range 1 to 5 advantageously 2 to 5 mm to enable it readily to be filled into the cavity but not to be washed out by exudation. It is possible in some instances for the granulate to be of such fine grain that it can be used post-operatively, for example when the exudate is found to be non-sterile being instilled by means of a syringe via a drain. Particle sizes less than 0.5 mm are preferred (e.g. about 0.4 mm) for this purpose.

The gel will normally contain a small quantity of free formaldehyde and this may be removed by washing until no further formaldehyde appears in the wash water; in order to avoid removing the antibacterial substance at the same time, the washing is preferably effected with an aqueous solution of the antibacterial substance. Testing using gas chromatography (GC-WLD or FID) can detect free formaldehyde down to 0.003%. As indicated above, the amount of formaldehyde added initially is greater than that finally bound in the gel, after washing. In general, 4% of formaldehyde (relative to protein) may be added initially to produce 2.7% bound formaldehyde. Where polyvinylpyrrolidone is added, the percentage of formaldehyde is preferably lower e.g. about 3%.

The gel takes at least 24 hours for solidification, but we have found that it is advantageous to leave the gel for a longer period than this before washing and (if desired) granulation. Thus, the gel should be left for at least 1 to 8 days, advantageously 4 to 7 days during which time its firmness is greatly improved due possibly to the continuance of cross-linking reactions within the gel. This procedure is particularly advantageous where the gel is to be provided in the form of a granulate as the increase in firmness improves the granulability of the gel.

As indicated above, cross-linking may be effected by methylol transfer antibacterial agents such as taurolidine, which itself is the preferred antibacterial due to its anti-endotoxaemic effects and absence of development of resistant pathogens. Thus, taurolidine may be incorporated at a level of about 4.75% into a solution of edible gelatin and left for several days. There is a slight fall in the level of active taurolidine for example to about 3.7%, but cross-linking occurs to yield a gel of satisfactory firmness. No washing is required for the removal of excess formaldehyde.

It has been found useful in certain circumstances to reduce the water content of the gel material by partial drying. The material may for example be dried to reduce the water content by 60–80%, e.g. about 70% by weight.

Drying may be effected by laying strips or sheets of gel in an oven or warm air cabinet at a temperature slightly above ambient, such as 30–50, e.g. about 40° C. Vacuum drying may be used as an alternative. The degree of dehydration should be carefully monitored, as it is not intended that the material should be completely dehydrated. Drying of the material in this way has been found to have the advantage of increasing the firmness and granulability of the gels.

If the gel is left in the form of rods or other shapes, these may conveniently be sterile packed in suitable water- and air- impermeable packaging material, such as sealable polyvinyl chloride or polyethylene foil sterilised, for instance, by washing with 70% aqueous isopropanol. The foil may be backed with paper and/or aluminium foil to increase water impermeability. If all the previous steps are effected under sterile conditions, no further sterilisation will be required. Otherwise sterilisation may be effected using ethylene oxide or formaldehyde. Thus, for example, the gel may be left, e.g. for about 20 days, with about 100 ppm ethylene oxide. The ethylene oxide level falls around this period to about 1–2 ppm due to hydrolysis and is subsequently removed. Sterility may be more readily maintained if an inner and an outer envelope packaging foil is used, the inner envelope only being taken into the operating theatre.

One particularly useful method of treatment according to the invention is to mix the gel in sterile granular form with autologous spongiosa tissue obtained from a healthy bone of the same patient. The iliac crest can provide small quantities of spongiosa tissue, while larger quantities can be obtained from the trochanter major and spina iliaca posterior. In this mode of use, it is essential that the gel should be isotonic, in order to avoid osmotic effects on contact with the spongiosa tissue. The aqueous phase of the gel can thus be physiological saline or Ringer lactate solution. (0.22% lactic acid, 0.6% NaCl, 0.4% KCl, 0.4% $CaCl_2 6H_2O$; neutralised with NaOH to be orange to phenol red indicator (pH 7.0), sterilised for 15 minutes at 12° C.) In general, the gels of the invention have colloid osmotic pressure compatible with the skin. The colloid osmotic pressure may be enhanced by incorporation of a low molecular weight polyvinylpyrrolidine, e.g. in the molecular weight range 8000–12,000 daltons, for example about 11,000 daltons. In that the salts in such solutions may affect the setting of the gel on cooling, they are preferably introduced after the gel has set, by including them in the washing solution used to remove formaldehyde. In order to accelerate incorporation of the salts into the gel, the concentrations of the salts in such wash water may be hypertonic and their uptake into the gel may be monitored until isotonicity is achieved. However, uptake is quite rapid from isotonic solutions.

Depending on the particular case of osteitis, provision may be made for drainage of the area. When healing is taking place rapidly, there is a healthy exudation of fluid. We have found that when using the method of the invention, there is normally observed an increase in such exudation which is, in fact, completely sterile. Furthermore, the cavity is found to heal particularly rapidly.

The gel according to the invention (10% gelatine containing 2% taurolidine) has been tested against experimentally induced osteomyelitis in foxhounds. The femur of the anaesthetised animal was opened up from the trochanter major, scraped out with a venoscleroticum and inoculated with 1 ml of an infective mixture isolated from an osteomyelitis in a dog, and consisting primarily of Proteus and coagulase-positive S. aureus strains. A steel rod was implanted as a foreign body to accelerate the infection. The course of the infection was monitored by X-ray and scintigraphic studies.

When the osteomyelitis was seen to be established, the femur was re-opened and the cavity filled with rods of cross-linked collagen gel, containing 2% taurolidine. The wound was then closed without drainage. The healing of the osteomyelitis was then monitored by X-ray and scintigraphic studies (TC99, 0.2 mCi/kg). Subsequently, the healed bone was subjected to bacteriological and histological examination.

The first dog studied was infected in the above way in the right femur and developed a classical osteomyelitis with a marked periostal reaction. In order to eliminate the possibility that the removal of the metal rod caused spontaneous healing, the rod was re-implanted. Bacteriological studies showed initially the presence of S.aureus and Proteus. Three weeks after the operation, the periostal reaction was still recognisable by X-ray studies but was already contracting. The difference in activity between the left and right legs, as shown in the scintigram was 3.98. After six weeks, X-ray studies showed further healing of the osteomyelitis. Scintigraphy then showed a ratio of right/left from 1.37 to 1.39 (two controls), close to a normal observation.

Six months later, the bone was sectioned:
Bacteriology: two samples were sterile.
Histology: scar plates which partially enclosed amorphous material. Spongiosa with active regeneration, wherein numerous osteoblast fringes could be seen. Between the partially destroyed bone trabeculae extended areas of scar plates which were vascularised at the periphery.

In the second animal, both femurs were infected, the left somewhat more strongly than the right. The left bone was treated as described above and filled with taurolidine-collagen rods and two months later, X-ray studies showed a contraction of the periostal reaction in the left bone, with simultaneous increase in the right. The activity ratio in the scintigram was correspondingly changed, the right/left ratio changing from 0.79 to 1.16.
Bacteriology of left femur:
 1. Scraping - no bacterial growth
 2. Scraping - no bacterial growth
Bacteriology of right femur: Proteus.
Histology of left femur: Marked cellular reaction; no foreign material, i.e. taurolidine gel resorbed, active regeneration of the bone trabeculae.
Histology of right femur: Showed a very marked osteomyelitis.

In the third animal, the right femur was infected while the left was only implanted with a metallic foreign body. The course of treatment with taurolidine-collagen rods was as previously, and was followed by X-ray and scintigraphic studies. The right/left ratio of the activity shown in the scintigram changed from 3.19 initially to 1.17 after three months.
Bacteriology:
 1. Scraping—no bacterial growth
 2. Scraping—no bacterial growth
Histology of right femur: Marked, cell poor, scar formation, which had built up between the still partially formed bone trabeculae. The scar-forming process had widely ceased.
Histology of left femur: Inflamed activity around the implanted foreign body.

The following examples are given by way of illustration only:

EXAMPLE 1

Edible gelatin (125 g) was dispersed in 1% aqueous taurolidine (1250 ml) for about 10 minutes and subsequently warmed to 60° C. with stirring. Aqueous formaldehyde (36%; 12 ml) was added to the liquid gel with stirring. The mixture was further stirred at 60° C. for 10–15 minutes and then poured into clean pre-heated polyvinylchloride tubes (diameter 14 mm). The tubes were cooled overnight and cut into 15 cm lengths and cut open. The transparent rods so obtained were then washed in a 1% taurolidine solution for about 4 hours in order to remove excess formaldehyde. The formaldehyde was quantitatively detected by gas chromatography (GC-WLD) and the washing was continued until no further free formaldehyde diffused into the wash water. The detection limit for free formaldehyde by this method was 0.003%.

A number of the rods were granulated in a Zyliss electric mincer, with sieve openings of 4.5 mm.

The rods as well as the granulate were then enclosed in a sealable polyethylene foil envelope backed with aluminium foil previously washed with 70% isopropanol. This may then be sealed in a second similar sterile envelope.

For the formation of the granulate, the gel mass can also be moulded in a larger vessel, such as a crystallisation dish, and on cooling the mass can be washed as above with 1% taurolidine solution and subsequently granulated in the electric mincer.

EXAMPLE 2

Gelatine rods were prepared according to the procedure of Example 1 but using 2% aqueous taurolidine in the formation of the gel and in the washing step and forming rods of diameter 10 mm and 15 mm.

EXAMPLE 3

The procedure of Example 1 was repeated using, in place of gelatin, 125 g of a mixture of gelatin and tropocollagen in the ratio 2:1. The tropocollagen was derived from animal skin (calf skin) with a molecular weight of approximately 130,000.

EXAMPLE 4

The procedure of Example 1 was repeated, using instead of the gelatin, a mixture of collagen fibres and gelatin in the weight ratio 1:3. The product was less transparent than that obtained using gelatin alone. The collagen fibres were added in a 10% suspension in water. A similar product was prepared using a mixture of collagen fibres and gelatin in the ratio 1:2, the overall concentration of gelatin being increased to 20% and the quantity of 36% aqueous formaldehyde being increased to 24 ml.

EXAMPLE 5

The procedure of Example 1 was repeated, but the washing step was carried out with 2% aqueous taurolidine containing isotonic Ringer lactate solution (0.22% lactic acid, 0.6% NaCl, 0.4% KCl, 0.4% $CaCl_2.6H_2O$; neutralised with NaOH to be orange to phenol red indicator; sterilised for 15 minutes at 120° C.)

After formulation of the gel into a granulate, this was mixed with an equal weight of freshly obtained spongiosa under sterile conditions and in an operation on an osteomyelitis of the femur, filled into the cavity created by removal of infected tissue. The wound was closed with provision of drainage and subsequently the wound healed well, the exudation from drainage being found to be sterile.

EXAMPLE 6

10 g edible gelatine was stirred for thirty minutes in 100 ml of 2% aqueous taurolidine solution containing 5% polyvinylpyrrolidone (PVP). The pH was adjusted to 7.0 with 25% aqueous NaOH. 1 g of a 36/37% formaldehyde aqueous solution was added and the mixture stirred for a further five minutes, after which time 25 g of dibasic calcium phosphate was added and stirring continued whilst the solution was allowed to cool.

The gel was left to stand for at least 4, preferably 4–7 days following which it was cut into pieces measuring about 2×3×3 cm and then washed using either (a) a solution of "Drainasept"/NaCl or (b) a solution of Ringer lactate plus 2% taurolidine in each case washing was carried out for four hours after which time the solution was changed and the gel washed in fresh solution for a further four hours.

The gel was finally washed with 2% taurolidine solution until isotonicity was achieved. The osmotic pressure of the gels was as follows:

before washing 200–400 mmol/kg after washing 280–320 mmol/kg, as measured by a 5100 vapour pressure osmometer supplied by Wescor Inc.

The gel was granulated in a mincing machine to about 1–2 mm in particle size. If desired the gels were placed in a homogeniser (e.g. "Homocenta") and ground very finely to permit of their being injected into the cavity via a suitable drain. Finally the granulated gel was placed in plastic containers previously washed with isopropanol.

EXAMPLE 7

Example 6 was repeated using the following ingredients:

|  | g |
| --- | --- |
| Taurolidine solution 2% (containing 5% PVP) | 100 |
| bone gelatin | 10 |
| 36/37% aqueous formaldehyde | 1 |
| dibasic calcium phosphate | 25 |

EXAMPLE 8

Example 6 was repeated using the following ingredients:

|  | g |
| --- | --- |
| Distilled water | 100 |
| Taurolidine | 2 |
| edible gelatin | 10 |
| 36/37% aqueous formaldehyde | 1 |
| dibasic calcium phosphate | 25 |

EXAMPLE 9

Example 6 was repeated using the following ingredients:

|  | g |
| --- | --- |
| Taurolidine solution 2% (containing 5% PVP) | 100 |
| bone gelatin | 10 |
| gentamycin sulphate | .15 |
| 36/37% aqueous formaldehyde | 1 |
| dibasic calcium phosphate | 25 |

EXAMPLE 10

Example 6 was repeated using the following ingredients:

|  | g |
| --- | --- |
| Taurolidine solution 2% (containing 5% PVP) | 100 |
| bone gelatin | 10 |
| chondroitin sulphate (sodium salt) | 2 |
| 36/37% aqueous formaldehyde | 1 |
| dibasic calcium phosphate | 25 |

EXAMPLE 11

Example 6 was repeated using the following ingredients:

|  | g |
| --- | --- |
| Taurolidine solution (containing 5% PVP) | 100 |
| bone gelatin | 10 |
| collagen (100%) | 2 |
| 36/37% aqueous formaldehyde | 1 |
| dibasic calcium phosphate | 25 |

EXAMPLE 12

Example 6 was repeated using the following ingredients:

|  | g |
| --- | --- |
| Taurolidine solution 2% | 100 |
| bone gelatin | 10 |
| 36/37% aqueous formaldehyde | 1 |
| dibasic calcium phosphate | 25 |

In this case the gel was left only for 1 to 4 days to set. Before washing as for Examples 1 to 6 the osmotic pressure of the gel was 300 mmol/kg. After washing it was 290 mmol/kg. The gel was granulated as before.

EXAMPLE 13

1000 ml of an aqueous solution comprising 2.55% taurolidine and 5% "Kollidon" K 17 PF (polyvinyl pyrrolidone) and distilled water to 1000 ml was warmed to 60° C. and 100 g edible gelatin (S.O.260) of 260–280 Bloom grams dissolved therein. The pH was adjusted to 7.0 with 25% NaOH. 7.5 g of a 35% aqueous formaldehyde solution ("Merck") was added and the mixture stirred for 15 minutes. The gel was allowed to stand for 7 days, after which it was washed for 9 hours in an equal weight of Ringer lactate solution containing 10% taurolidine followed by 60 hours in fresh solution. The gel was granulated as before.

EXAMPLE 14

Example 13 was repeated using the following ingredients:

|  | g |
| --- | --- |
| taurolidine solution 4.75% | 1000 |
| edible gelatin S.o. 260 | 100 |
| 35% aqueous formaldehyde ("Merck"). | 7.5 |

(The taurolidine solution used contained:

|  | g |
| --- | --- |
| "Kollidon" K 17 PF (polyvinylpyrrolidone) | 5 |
| taurolidine | 4.75 |
| Distilled water | to 100 |

EXAMPLE 15

Example 14 was repeated but omitting the washing step.

EXAMPLE 16

2.0 g taurolidine were dissolved at 60° C. in 94 g distilled water and, after cooling to room temperature, 1.5 g of lactic acid (approx. 91%) were added and the pH adjusted to 7.0 with 25% aqueous sodium hydroxide. 0.024 g potassium chloride, 0.024 g calcium chloride hexahydrate and 0.33 g sodium chloride were added. The solution was heated to 60° C. and 2 g edible gelatin dispersed therein. The pH was adjusted to 7.0 with 25% NaOH. 0.035 g of 100% formaldehyde were than added and the solution stirred until completely clear. The solution was poured into an infusion flask (250 ml) and autoclaved for 20 minutes at 120° C.

EXAMPLE 17

4.0 g taurolidine were dissolved in 100 g distilled water and 10 g edible gelatin dispersed with stirring. The pH was adjusted to 7.0 with 25% NaOH. The solution was warmed to 60° C. for 10–15 minutes and poured into pre-heated polyvinylchloride tubes (diameter 14 mm). The tubes were allowed to stand for several days and then cut open. The transparent rods so obtained were found to have a firmness similar to that of gels obtained by cross-linking using formaldehyde. A small quantity of taurinamide was detected, indicating methylol transfer by the taurolidine.

EXAMPLE 18

Example 16 was repeated using 4.75 g taurolidine and 5 g PVP.

I claim:

1. A composition for the treatment of osteitis comprising a flexible solid in granular form adapted to be introduced into a bone cavity, the said solid comprising a resorbable aqueous gel of one or more cross-linked fibrous proteins having dissolved or dispersed therein an antibacterially effective amount of one or more water-soluble antibacterial medicaments.

2. A composition as claimed in claim 1 wherein the gel comprises cross-linked gelatin.

3. A composition as claimed in claim 1 wherein the protein is cross-linked by a methylol-transfer agent.

4. A composition as claimed in claim 3 wherein the methylol transfer agent comprises formaldehyde.

5. A composition as claimed in claim 1 wherein the antibacterial medicament comprises an antibiotic.

6. A composition as claimed in claim 1 wherein the flexible solid is in the form of a granulate in admixture with spongiosa tissue.

7. A composition as claimed in claim 1 wherein the flexible solid is in the form of a rod.

8. A method of treating osteitis which comprises introducing into a bone cavity infected with osteitis a flexible solid as claimed in claim 1 and allowing it to remain there until resorbed.

9. A composition as claimed in claim 1 wherein the antibacterial medicament comprises a methylol-transfer antibacterial agent.

* * * * *